(12) United States Patent
Sangwai et al.

(10) Patent No.: US 9,958,367 B2
(45) Date of Patent: May 1, 2018

(54) APPARATUS FOR MEASURING RHEOLOGICAL PARAMETERS AND METHODS FOR ITS OPERATION

(71) Applicant: INDIAN INSTITUTE OF TECHNOLOGY MADRAS, Chennai, Tamil Nadu (IN)

(72) Inventors: Jitendra Sangwai, Mehekar (IN); Chirag Khalde, Talegaon Dabhade (IN)

(73) Assignee: INDIAN INSTITUTE OF TECHNOLOGY MADRAS, Chennai (IN)

( * ) Notice: Subject to any disclaimer, the term of this patent is extended or adjusted under 35 U.S.C. 154(b) by 16 days.

(21) Appl. No.: 14/783,811

(22) PCT Filed: Apr. 9, 2014

(86) PCT No.: PCT/IB2014/060545
§ 371 (c)(1),
(2) Date: Oct. 9, 2015

(87) PCT Pub. No.: WO2014/167503
PCT Pub. Date: Oct. 16, 2014

(65) Prior Publication Data
US 2016/0054213 A1 Feb. 25, 2016

(30) Foreign Application Priority Data
Apr. 9, 2013 (IN) .......................... 1610/CHE/2013

(51) Int. Cl.
*G01N 11/14* (2006.01)
*G01N 33/28* (2006.01)
(Continued)

(52) U.S. Cl.
CPC ............. *G01N 11/00* (2013.01); *G01N 11/14* (2013.01); *F04C 2/22* (2013.01); *F04C 18/16* (2013.01);
(Continued)

(58) Field of Classification Search
CPC ....... G01N 11/14; G01N 33/28; F01C 21/002; F04C 11/001; F04C 13/001; F04C 13/008;
(Continued)

(56) References Cited

U.S. PATENT DOCUMENTS 4,095,461 A 6/1978 Starita
4,638,668 A 1/1987 Leverberg et al.
(Continued)

FOREIGN PATENT DOCUMENTS

CH 683322 A5 2/1994
GB 660662 A 11/1951
(Continued)

OTHER PUBLICATIONS

International Search Report and Written Opinion for International Application No. PCT/IB14/60545, dated Sep. 10, 2014.
(Continued)

*Primary Examiner* — Randy Gibson
*Assistant Examiner* — Gedeon M Kidanu
(74) *Attorney, Agent, or Firm* — Maschoff Brennan

(57) ABSTRACT

An apparatus for measuring rheological parameters of a multi-phase fluid is provided. The apparatus includes a static chamber containing a multi-phase fluid having at least a first phase and a second phase. The apparatus also includes a rotor member submersed in the multiphase fluid in the static chamber. The rotor member includes a first set of threads formed on a first portion of the rotor member submersed in the first phase of the multi-phase fluid and a second set of
(Continued)

threads formed on a second portion of the rotor member submersed in the second phase of the multi-phase fluid.

31 Claims, 7 Drawing Sheets

(51) Int. Cl.
*F04C 18/16* (2006.01)
*F04C 2/22* (2006.01)
*G01N 11/00* (2006.01)

(52) U.S. Cl.
CPC ...... *G01N 33/28* (2013.01); *G01N 2011/0033* (2013.01)

(58) Field of Classification Search
CPC ...... F04C 14/26; F04C 18/16; F04C 2210/24; F04C 2240/81; F04C 2270/17; F04C 29/0014; F04C 2/16
USPC ............ 73/54.01–51.02, 54.23, 54.28, 54.31
See application file for complete search history.

(56) References Cited

U.S. PATENT DOCUMENTS

| | | | |
|---|---|---|---|
| 4,643,021 A | 2/1987 | Mattout | |
| 4,684,072 A * | 8/1987 | Nelson | B02C 17/04 241/171 |
| 4,878,377 A * | 11/1989 | Abel | G01N 11/14 73/54.32 |
| 4,974,446 A | 12/1990 | Vigneaux | |
| 5,209,108 A * | 5/1993 | Shackelford | E21B 43/26 73/54.28 |
| 5,348,453 A * | 9/1994 | Baran | B29C 47/0845 417/440 |
| 5,365,777 A | 11/1994 | Layton | |
| 5,728,951 A | 3/1998 | Van Cleve et al. | |
| 6,135,723 A * | 10/2000 | Hatton | F04C 2/16 417/251 |
| 6,234,030 B1 * | 5/2001 | Butler | E21B 21/01 73/195 |
| 6,629,451 B1 * | 10/2003 | Taylor | G01N 11/14 73/54.28 |
| 6,691,560 B2 | 2/2004 | Abnett | |
| 6,742,774 B2 | 6/2004 | Hall | |
| 6,874,353 B2 * | 4/2005 | Johnson | G01N 11/14 73/54.01 |
| 6,959,588 B2 | 11/2005 | Zougari et al. | |
| 6,971,262 B1 | 12/2005 | Marchal et al. | |
| 6,997,045 B2 | 2/2006 | Wallevik et al. | |
| 7,017,393 B2 | 3/2006 | Doe et al. | |
| 7,021,123 B2 | 4/2006 | Wallevik et al. | |
| 7,581,436 B2 | 2/2009 | Eskin et al. | |
| 8,024,962 B2 | 9/2011 | Tonmukayakul et al. | |
| 8,794,051 B2 * | 8/2014 | Morgan | G01N 11/14 73/54.01 |
| 2002/0004176 A1 * | 1/2002 | Tanabe | G03G 9/0804 430/137.14 |
| 2003/0154772 A1 | 8/2003 | Jackson | |
| 2003/0192366 A1 | 10/2003 | Taylor | |
| 2005/0170516 A1 | 8/2005 | Kharrat et al. | |
| 2005/0284212 A1 | 12/2005 | Marchal et al. | |
| 2009/0133478 A1 * | 5/2009 | Sentmanat | G01N 11/14 73/54.28 |
| 2011/0020162 A1 | 1/2011 | Izawa et al. | |
| 2011/0061451 A1 | 3/2011 | Harris et al. | |
| 2011/0123378 A1 | 5/2011 | Kothnur et al. | |
| 2011/0293441 A1 * | 12/2011 | Anderson | F01C 21/002 417/279 |
| 2013/0136639 A1 * | 5/2013 | Simpson | F04D 3/02 418/1 |

FOREIGN PATENT DOCUMENTS

| | | |
|---|---|---|
| GB | 711851 A | 7/1954 |
| WO | 2008154035 A1 | 12/2008 |

OTHER PUBLICATIONS

Lord, D.L., "Helical Screw Rheometer: A New Tool for Stimulation Fluid Evaluation," Society of Petroleum Engineers, pp. 7 (1988).
Lord, D.L., and Shackelford, D., "Application of Helical Screw Rheometer for Rheological Measurements," Petroleum Society of Canada, vol. 29, Issue 3, pp. 6 (May 1990).
International Search Report and Written Opinion for International Application No. PCT/IB2014/063868, dated Feb. 6, 2015, pp. 10.
Extended European Search Report dated Dec. 1, 2016 as received in Application No. 14782984.0.

* cited by examiner ated on Apr. 9, 2014, which claims priority
APPARATUS FOR MEASURING RHEOLOGICAL PARAMETERS AND METHODS FOR ITS OPERATION

CROSS-REFERENCE TO RELATED APPLICATIONS

This application is a U.S. National Stage filing under 35 U.S.C. § 371 of International Patent Application No. PCT/IB2014/060545, filed on Apr. 9, 2014, which claims priority from Indian Patent Application No. 1610/CHE/2013, filed on Apr. 9, 2013, and entitled "Apparatus for Measuring Rheological Parameters and Methods for its Operation", the contents of which are incorporated herein in their entireties.

BACKGROUND

Various types of fluids are used in applications in upstream oil and gas industry, paint industry, polymer industry, pharmaceutical industry, etc. Understanding rheology of emulsions, slurries and suspensions is desirable in these applications. Typically, as two or more immiscible fluids flow through a pipeline, the mixing of the fluids varies at different locations within the pipeline due to varying shear rates. This flow phenomenon may result in formation of emulsions and suspensions that are substantially stable in shear environment but may separate as the effect of shear is reduced. It is desirable to determine rheological parameters such as viscosity, elasticity, and consistency for such fluids.

Conventional techniques for measuring the rheological properties of multi-phase fluids such as emulsion and slurries include mixing them in a separate pre-mixer. The emulsion formed after the mixing is subsequently transferred to a cup and bob assembly of a rheometer and the viscosities may be measured using the rheometer for different shear rates. However, mixing of the fluids using the conventional cup and bob systems is poor especially at low shear rates. Moreover, pre-mixed emulsions are substantially unstable.

Moreover, such systems use cup and bob with plain surfaces that do not provide enhanced mixing for multi-phase fluids. Therefore, such systems require substantially stable emulsions and slurries for rheology measurements. Moreover, as the pre-mixing is done in a mixer and the sample is subsequently transferred to rheometer the two mixed phases may have a propensity to separate during the rheological measurements. This may result in inaccurate measurements. Improved apparatus for measuring rheological parameters of multi-phase fluids and methods of their operation are desirable.

SUMMARY

The foregoing summary is illustrative only and is not intended to be in any way limiting. In addition to the illustrative aspects, embodiments, and features described above, further aspects, embodiments, and features will become apparent by reference to the drawings and the following detailed description.

Briefly, in accordance with one aspect, an apparatus for measuring rheological parameters of a multi-phase fluid is provided. The apparatus includes a static chamber containing a multi-phase fluid having at least a first phase and a second phase. The apparatus also includes a rotor member submersed in the multiphase fluid in the static chamber. The rotor member includes a first set of threads formed on a first portion of the rotor member submersed in the first phase of the multi-phase fluid and a second set of threads formed on a second portion of the rotor member submersed in the second phase of the multi-phase fluid.

In accordance with another aspect, an apparatus for measuring rheological parameters of a multi-phase fluid is provided. The apparatus includes a static chamber containing a multi-phase fluid having at least a first phase and a second phase. The apparatus also includes a rotor member submersed in the multi-phase fluid in the static chamber and rotatable about a rotational axis within the static chamber to apply a shear stress to the multi-phase fluid. The rotor member includes a first portion having a first set of threads formed thereon in a first direction and a second portion having a second set of threads formed thereon in a second direction that is opposite to the first direction. The apparatus further includes a processing circuitry configured to estimate the rheological parameters of the multi-phase fluid as the rotor member is rotated within the static chamber.

In accordance with another aspect, a method for measuring rheological parameters of a multi-phase fluid is provided. The method includes providing a static chamber having a rotor member where the rotor member includes a first portion having a first set of threads formed thereon in a first direction and a second portion having a second set of threads formed thereon in a second direction that is opposite to the first direction. The method includes placing a multi-phase fluid having a first phase and a second phase within the static chamber such that the first portion and the second portion of the rotor member are substantially submersed in the first phase and the second phase of the multi-phase fluid respectively. The method also includes rotating the rotor member about a rotational axis to apply shear stress to the first phase and the second phase of the multi-phase fluid through the first set of threads and the second set of threads respectively.

In accordance with another aspect, a kit is provided. The kit includes a rotor member having at least a first portion and a second portion with a first set of threads and a second set of threads formed thereon respectively. The first set of threads and the second set of threads are oppositely angled and are configured to apply a shear stress to a first phase and a second phase of a multi-phase fluid as the rotor member is rotated inside a static chamber containing the multi-phase fluid.

DETAILED DESCRIPTION

Figure 1:
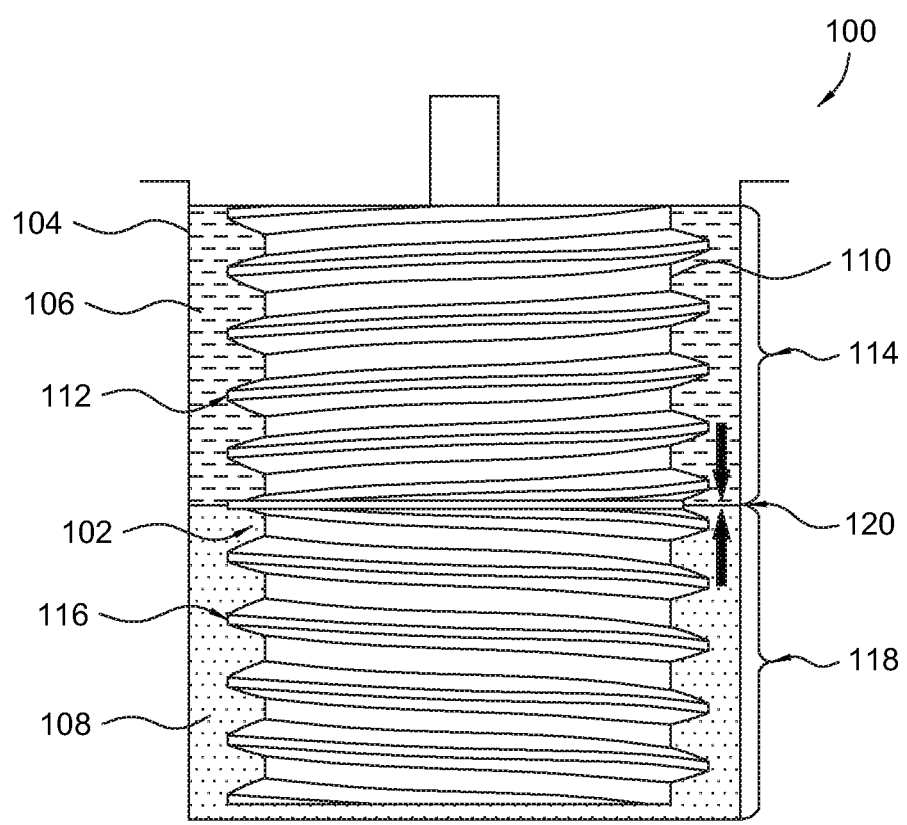
FIG. 1 is an example apparatus for measuring rheological parameters of a multi-phase fluid.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

It will also be understood that any compound, material or substance which is expressly or implicitly disclosed in the specification and/or recited in a claim as belonging to a group or structurally, compositionally and/or functionally related compounds, materials or substances, includes individual representatives of the group and all combinations thereof. While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

Some embodiments are generally directed to techniques of measuring rheological parameters of multi-phase fluids like emulsions, slurries and suspensions such as used in upstream oil and gas, paint, polymer and pharmaceutical industries. The embodiments described below provide an apparatus that enhances mixing of multi-phase fluids and facilitates accurate measurement of rheological parameters of fluids. The proposed technique can be used for rheological measurements of complex fluids at high pressure and high temperature conditions such as required in oil and gas industries.

The proposed apparatus provides a threaded rotor member that is used for mixing fluids within a static chamber. In particular, the rotor member includes oppositely angled threads that facilitate mixing of the fluids. As the rotor member rotates within the static chamber with the fluids, it applies shear stress to the fluids through the oppositely angled threads thereby driving the fluids towards an interface of the fluids thereby resulting in enhanced mixing as compared to conventional cup and bob rheometers having un-threaded rotor member with smooth surfaces.

Referring now to FIG. 1 an example, apparatus 100 for measuring rheological parameters of a multi-phase fluid 102 is provided. The apparatus includes a static chamber 104 containing the multi-phase fluid 102 having at least a first phase 106 and a second phase 108. In certain embodiments, the multi-phase fluid 102 includes at least two immiscible fluids. In one example embodiment the two immiscible fluids are oil and water. In one example embodiment, the first phase 106 of the multi-phase fluid 102 is a liquid and the second phase 108 is a gas. In another example embodiment, the first phase 106 of the multi-phase fluid 102 is a solid and the second phase 108 is a liquid. In certain embodiments, the multi-phase fluid 102 may include more than two phases. For example, the first phase 106 of the multi-phase fluid 102 can include a liquid, the second phase 108 can include a solid and a third phase (not shown) of the multi-phase fluid 102 can be a gas.

The static chamber 104 may be formed of metal, steel, stainless steel, hastelloy, titanium, aluminum, quartz, optical glass, inconel, or combinations thereof. However, a variety of other materials may be used for the static chamber 104. The static chamber 104 can generally be of any size. The size of the static chamber 104 may be selected based upon viscosity of the multi-phase fluid 102, density of the multi-phase fluid 102, an applied shear rate, or combinations thereof.

The apparatus 100 further includes a rotor member 110 submersed in the multi-phase fluid 102 in the static chamber 104. The rotor member 110 is rotatable about a rotational axis within the static chamber 104. In this example embodiment, the static chamber 104 and the rotor member 110 are arranged to be coaxial. The rotor member 110 may be formed of metal, steel, stainless steel, hastelloy, titanium, aluminum, quartz, optical glass, inconel, or combinations thereof. Other suitable materials may be used for the rotor member 110. The apparatus 100 may include a motor (not shown) configured to rotate the rotor member 110 about the rotational axis within the static chamber 104.

The rotor member 110 may generally be of any size. The rotor member 110 may be designed based on DIN standards (DIN 53019 and 53018) and can have a diameter of about 10 mm to about 39 mm. The length of the rotor member 110 may be about three times the radius of the rotor member 110. In some examples, a ratio of the radius of the static chamber 104 to radius of the rotor member 110 is about 1.1. In certain examples, the diameter of the static chamber 104 is up to about 60 mm and the diameter of the rotor member 110 is about 50 mm.

In the illustrated embodiment, the rotor member 110 includes a first set of threads 112 formed on a first portion 114 of the rotor member 110 submersed in the first phase 106 of the multi-phase fluid 102. Moreover, the rotor member 110 includes a second set of threads 116 formed on a second portion 118 of the rotor member 110 submersed in the second phase 108 of the multi-phase fluid 102.

In the illustrated embodiment, the first set of threads 112 and the second set of threads 116 are oppositely angled. In one example embodiment, a thread angle of the first set of threads 112 and the second set of threads 116 is about 5 degrees (°) to about 70°. Specific examples of the thread angle of the first set of threads 112 and the second set of threads 116 include about 5°, about 10°, about 20°, about 25°, about 30°, about 35°, about 40°, about 45°, about 50°, about 55°, about 60°, about 65°, about 70°, and ranges between any two of these values (including endpoints).

The first set of threads 112 and the second set of threads 116 may have any desired configuration. For example, the first set of threads 112 and the second set of threads 116 may include acme threads, buttress threads, whitworth threads, V-threads, or combinations thereof. The pitch and depth of the first set of threads 112 and the second set of threads 116 may be selected based upon density and viscosity of each of the first phase 104 and the second phase 106 of the multiphase fluid 102 and a required degree of mixing of the first phase 104 and the second phase 106, or combinations thereof.

In some examples, the pitch of the first set of threads 112 and the second set of threads 116 is about 0.1 millimeter (mm) to about 25 mm. Specific examples of pitch of the first set of threads 112 and the second set of threads 116 include about 0.1 mm, about 0.5 mm, about 1 mm, about 2.5 mm, about 5 mm, about 7.5 mm, about 10 mm, about 12.5 mm, about 15 mm, about 17.5 mm, about 20 mm, about 22.5 mm, about 25 mm, and ranges between any two of these values (including endpoints). In some examples, a ratio of pitch of the first set of threads 112 and the second set of threads 116 to the length of the rotor member 110 is about 0.01 to 0.5. Specific examples of the ratio include about 0.01, about 0.05, about 0.1, about 0.15, about 0.2, about 0.25, about 0.3, about 0.35, about 0.4, about 0.45, about 0.5, and ranges between any two of these values (including endpoints).

In some examples, a depth of the first set of threads 112 and the second set of threads 116 is about 0.1 mm to about 25 mm. Specific examples of the depth of the first set of threads 112 and the second set of threads 116 include about 0.1 mm, about 1 mm, about 5 mm, about 10 mm, about 15 mm, about 20 mm, about 25 mm, and ranges between any two of these values (including endpoints). In some examples, a ratio of depth and the diameter of the first set of threads 112 and the second set of threads 116 is about 0.01 to about 0.5. Specific examples of the ratio of depth and the diameter of the first set of threads 112 and the second set of threads 116 include about 0.01, about 0.05, about 0.1, about 0.15, about 0.2, about 0.25, about 0.3, about 0.35, about 0.4, about 0.45, about 0.5, and ranges between any two of these values (including endpoints).

In operation, the rotor member 110 is rotated within the static chamber 104 and the first set of threads 112 and the second set of threads 116 formed on the rotor member 110 facilitate mixing of the first phase 104 and the second phase 106 of the multi-phase fluid 102. In particular, the static chamber 104 and the rotor member 110 define a shear zone containing the multi-phase fluid 102. The rotor member 110 rotates about the rotational axis to apply shear stress to the first phase 104 and the second phase 106 of the multi-phase fluid 102 through the first set of threads 112 and the second set of threads 116. The rotor member 110 facilitates driving of the first phase 104 and the second phase 106 of the multi-phase fluid 102 towards an interface 120 of the first portion 114 and the second portion 118 of the rotor member 110 to facilitate mixing of the first phase 104 and the second phase 106.

The oppositely angled first and second set of threads 112 and 116 facilitate and enhance the mixing of the first phase 104 and the second phase 106 of the multi-phase fluid 102. The system 100 therefore does not require a pre-mixer for mixing the first phase 104 and the second phase 106. Further, the apparatus facilitates formation of an emulsion or suspension even at low shearing rates. In certain embodiments, a degree of mixing of the first phase 104 and the second phase 106 may be controlled based upon a type of threads formed on the rotor member 110, number of threads and an applied shear rate through the rotor member 110.

In some example embodiments, a speed of rotation of the rotor member 110 is about 0.01 revolutions per minute (rpm) to about 10000 rpm, about 1 rpm to about 1,000 rpm, or about 10 rpm to about 100 rpm. Specific examples of speed of rotation include about 0.01 rpm, about 0.1 rpm, about 1 rpm, about 10 rpm, about 100 rpm, about 1,000 rpm, about 10,000 rpm, and ranges between any two of these values (including endpoints). In some examples, an applied shear rate is about $10^{-5}$ $S^{-1}$ to about $10^7$ $S^{-1}$.

In certain embodiments, a degree of mixing of the first phase 104 and the second phase 106 is about 1% to about 99%, and ideally 100%. Specific examples of the degree of mixing for first phase and second phase include about 1%, about 10%, about 20%, about 30%, about 40%, about 50%, about 60%, about 70%, about 80%, about 90%, about 99%, and ranges between any two of these values (including endpoints).

The apparatus 100 further includes a processing circuitry (not shown) configured to estimate the rheological parameters of the multi-phase fluid 102 based on an applied shear rate, temperature of the multi-phase fluid 102, pressure of the multi-phase fluid 102, or combinations thereof. Examples of the rheological parameters of the multi-phase fluid 102 include, but are not limited to, a viscosity ($\eta$), a shear storage modulus (G'), a shear loss modulus (G"), or combinations thereof.

A variety of configurations of the apparatus 100 described above may be envisaged. For example, the apparatus 100 may include the static chamber 104 with a plurality of threads formed on an inner surface of the static chamber 104 and the rotor member 110 having a smooth surface. In another example embodiment, the static chamber 104 containing the multi-phase fluid 102 is rotated about the rotational axis and the rotor member 110 is kept stationary within the rotating static chamber 104. In certain embodiments, the apparatus 100 can include double or multiple start threads on each of the static chamber 104 and the rotor member 110. Further, the apparatus 100 may be used for parallel plate geometry, cone geometry and plate geometry. The apparatus 110 can also be used for double gap geometry with proposed threading on the rotor member 110, the static chamber 102, or both.

Figure 2:
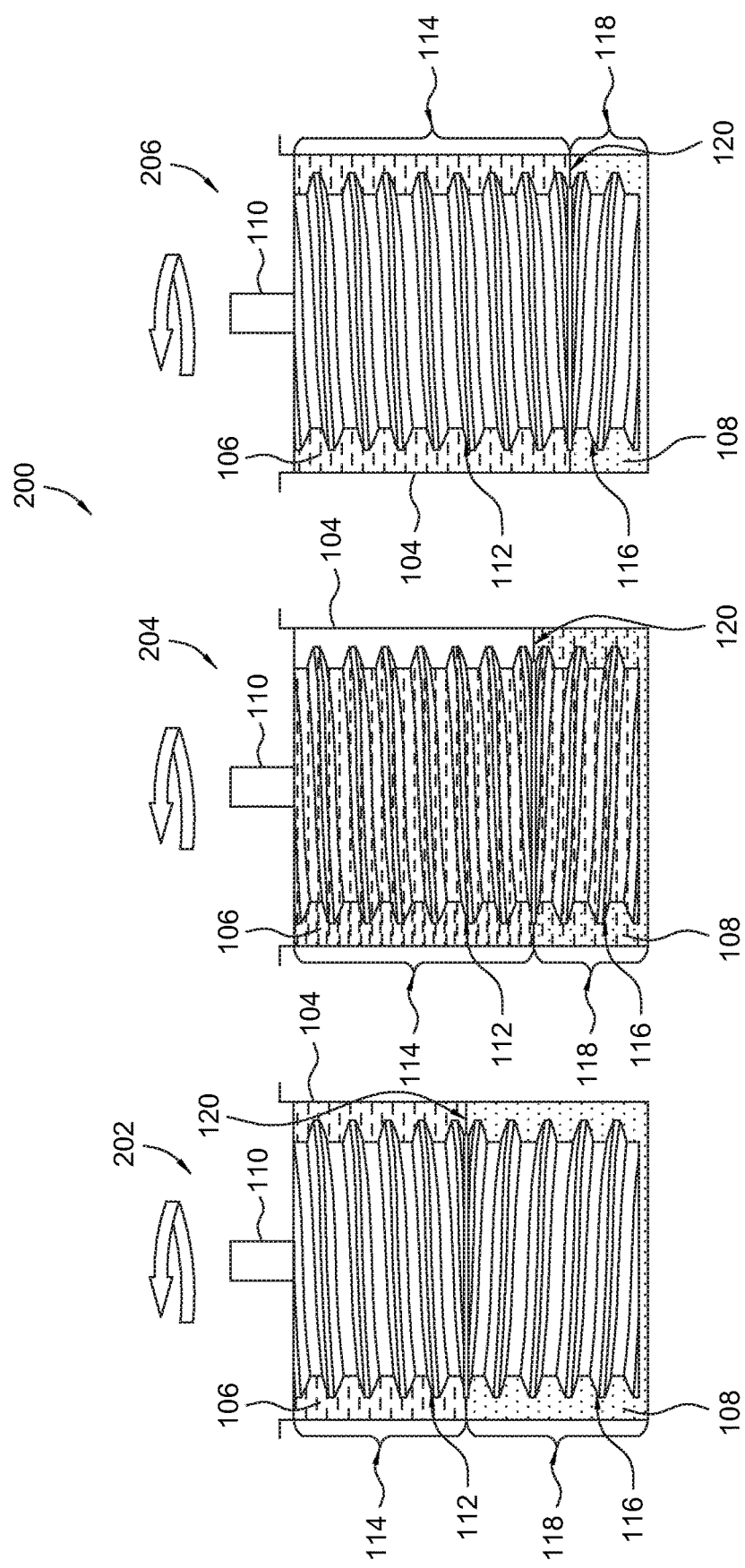
FIG. 2 illustrates example configurations of the apparatus of FIG. 1.

FIG. 2 illustrates example configurations 200 of the apparatus 100 of FIG. 1. As illustrated, each of the configurations represented by reference numerals 202, 204 and 206, includes the static chamber 104 and the rotor member 110 having a plurality of threads formed on a periphery of the rotor member 110. In the illustrated embodiment, the rotor member 110 includes the first set of threads 112 and the second set of threads 116 that are oppositely angled. Here, a height of the first portion 114 and the second portion 118 having the first set of threads 112 and the second set of threads 116 respectively is selected based upon a volume of the first phase 106 and the second phase 108 of the multi-phase fluid 102.

In the example configuration 202, the volume of first phase 106 of the multi-phase fluid 102 is substantially same as the volume of the second phase 108 of the multi-phase fluid 102. In this configuration, the height of the first portion 114 and the height of second portion 118 of the rotor member 110 are maintained to be substantially same and the transition from the first set of threads 112 of the first portion 114 to the second set of threads 116 of the second portion 118 of the rotor member 110 is made adjacent to the center of the rotor member 110.

In the example configuration 204, the volume of the first phase 106 of the multi-phase fluid 102 is about 70 percent (%) of the total volume of the multi-phase fluid 102 and the volume of the second phase 108 is about 30% of the total volume of the multi-phase fluid 102. In this configuration, the height of the first portion 114 is maintained at about ⅔ of the total height of the rotor member 110 and the height of second portion 118 of the rotor member 110 is maintained at about ⅓ of the total height of the rotor member 110.

In the example configuration 206, the volume of first phase 106 is about 80% of the total volume of the multi-phase fluid 102 and the volume of the second phase 108 is about 20% of the volume of the multi-phase fluid 102. In this configuration, the height of the first portion 114 is maintained at about ⅘ of the total height of the rotor member 110 and the height of second portion 118 of the rotor member 110 is maintained at about ⅕ of the total height of the rotor member 110.

It should be noted that a variety of such configurations with different heights of the first and second portions 114 and 118 of the rotor member 110 may be envisaged. The height of the first and second portions 114 and 118 may be selected based upon the volume of each of the first phase 106 and the second phase 108 of the multi-phase fluid 102, a type of the first phase 106 and the second phase 108, a viscosity of the first phase 106 and the second phase 108, among others. The unidirectional rotation of the rotor member 110 relative to the static chamber 104 coupled with the oppositely angled first and second sets of threads 112 and 116 results in a forced shear flow and enhanced mixing at the interface 120 of the oppositely angled threads.

Figure 3:
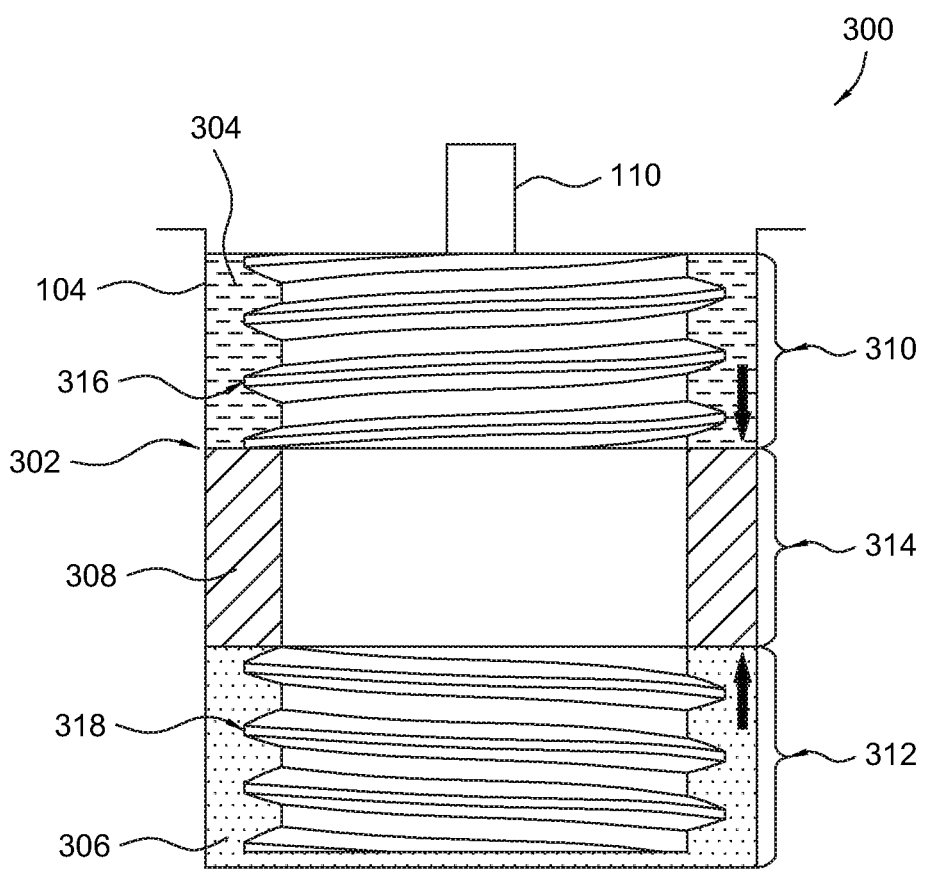
FIG. 3 illustrates an example configuration of an apparatus used for measuring rheological parameters of a multi-phase fluid having three phases.

FIG. 3 illustrates an example configuration 300 of the apparatus used for measuring rheological parameters of a multi-phase fluid 302 having three phases. In the illustrated embodiment, the multi-phase fluid 302 includes a first phase 304, a second phase 306 and a third phase 308. In one example, the first phase 304 is a liquid, the second phase 306 is a solid and the third phase 308 is a gas. Here, the rotor member 110 includes a first portion 310, a second portion 312 and a third portion 314. In one example embodiment, a volume of each of the first phase 304, the second phase 306 and the third phase 308 is substantially same. In this embodiment, a height of each of the first portion 310, the second portion 312 and the third portion 314 is substantially the same.

In this example, the first portion 310 includes a first set of threads 316 and the second portion 312 includes a second set of threads 318. The first set of threads 316 and the second set of threads 318 are oppositely angled. Further, the third portion 314 is un-threaded and is substantially dispersed in the third phase 308. The first set of threads 316 and the second set of threads 318 facilitate driving of the first phase 304 and the second phase 306 phases towards the third portion 314 thereby resulting in convergence of flows and efficient mixing in the central region of the rotor member 110.

The pitch for the first set of threads 316 and the second set of threads 318 of the rotor member 110 can vary depending on a degree of mixing required and the densities of the first phase 304, second phase 306 and the third phase 308 of the multi-phase fluid 302. The first set of threads 316 and the second set of threads 318 may have any desired configuration. For example, the first set of threads 316 and the second set of threads 318 may include acme threads, buttress threads, whitworth threads, V-threads, or combinations thereof.

EXAMPLES

The present invention will be described below in further detail with examples and comparative examples thereof, but it is noted that the present invention is by no means intended to be limited to these examples.

Example 1

Configuration of an Apparatus for Measuring Rheological Parameters of a Multi-Phase Fluid An apparatus having the configuration of FIG. 1 was used for measuring rheological parameters of a multi-phase fluid. Here, a rheometer commercially available from Anton Parr GmbH, Austria was used for measuring the rheological parameters of the multi-phase fluid. The apparatus had a rotor member having the first set of threads and the second set of threads placed within the static chamber. The static chamber included a jacket for circulation of hot and cold water through a water inlet and a water outlet to maintain a desired temperature of the multi-phase fluid within an annular space between the static chamber and the rotor member.

Here, different sizes of the static chamber and the rotor member were used for measuring the rheological parameters of the multi-phase fluid. The static chamber had a length of about 75 mm and a diameter of the static chamber was about 75 mm. The dimensions of the rotor member with the details of the threads formed on the rotor member are provided in Table 1. A standard geometry of the rotor member (represented here by M0) was obtained and used for obtaining viscosity measurements. Further, two configurations of the rotor member (represented by M1 and M2 respectively) with threads such as described with reference to FIG. 1 having different thread pitch and width were designed. The rotor member was formed of stainless steel-316.

TABLE 1

| Sr. No. | Rotor member length, L, mm | Rotor member diameter, D, mm | $L_1$, mm | Angle, θ | Half length from top, $L_2$ | Pitch, mm | Pitch Depth, d, mm | Nomenclature used |
|---|---|---|---|---|---|---|---|---|
| 1. | 38 | 25 | 7 | 30° | — | — | — | M0 |
| 2. | 38 | 25 | 7 | 30° | 19 | 1.5 | 1.0 | M1 |
| 3. | 38 | 25 | 7 | 30° | 19 | 3.0 | 2.0 | M2 |

The three configurations (M0, M1 and M2) of the rotor member were used to measure rheological parameters of emulsions. The comparative results for the measurements for the configurations with and without the first and second set of threads will be discussed below.

Example 2

Viscosity Measurements of Emulsions Using the Apparatus of Example 1

The apparatus of Example 1 was used to measure rheological parameters of emulsions. Here, viscosity of a water based fluid and an oil based fluid were measured using the standard geometry (M0) of the rotor member. The viscosity for the water based fluid and the oil based fluid were measured to be 10.12 centipoise (cP), and, 9.23 cP, respectively. The two fluids were subsequently used to form an emulsion in the annular space between the static chamber and the rotor member. The volume of the emulsion sample taken for the measurement of viscosity was about 16 milliliters (ml). A volume percentage of about 50:50 of the water based fluid and the oil based fluid was taken to form the multi-phase fluid for measurement of viscosity of the multi-phase fluid.

Example 3

Results of Viscosity Measurements of the Emulsion with Varying Shear Rates Applied Using the Rotor Members of Example 1

Here, standard viscosity fluids (referred herein as "calibrating fluids") with varying viscosities, such as, 4.5 cP, 98 cP, and 1000 cP at about 25° C. were obtained and were used to calibrate the various rotor member geometries of the apparatus of Example 1. The water based fluid and the oil based fluid were independently introduced into the static chamber of the apparatus. Moreover, water from high precision water bath was circulated from the jacket of the static chamber to maintain the temperature of the fluid at about 25° C. The rotor member corresponding to each of the configurations M0(without the threads), M1 (with threads), M2 (with threads), was placed in the static chamber and was rotated about a rotational axis within the static chamber. Further, viscosity measurements were estimated using the motor torque required to maintain a certain rotational speed of the rotor member in the emulsion. The viscosity measurements obtained using these configurations are discussed below.

Figure 4:
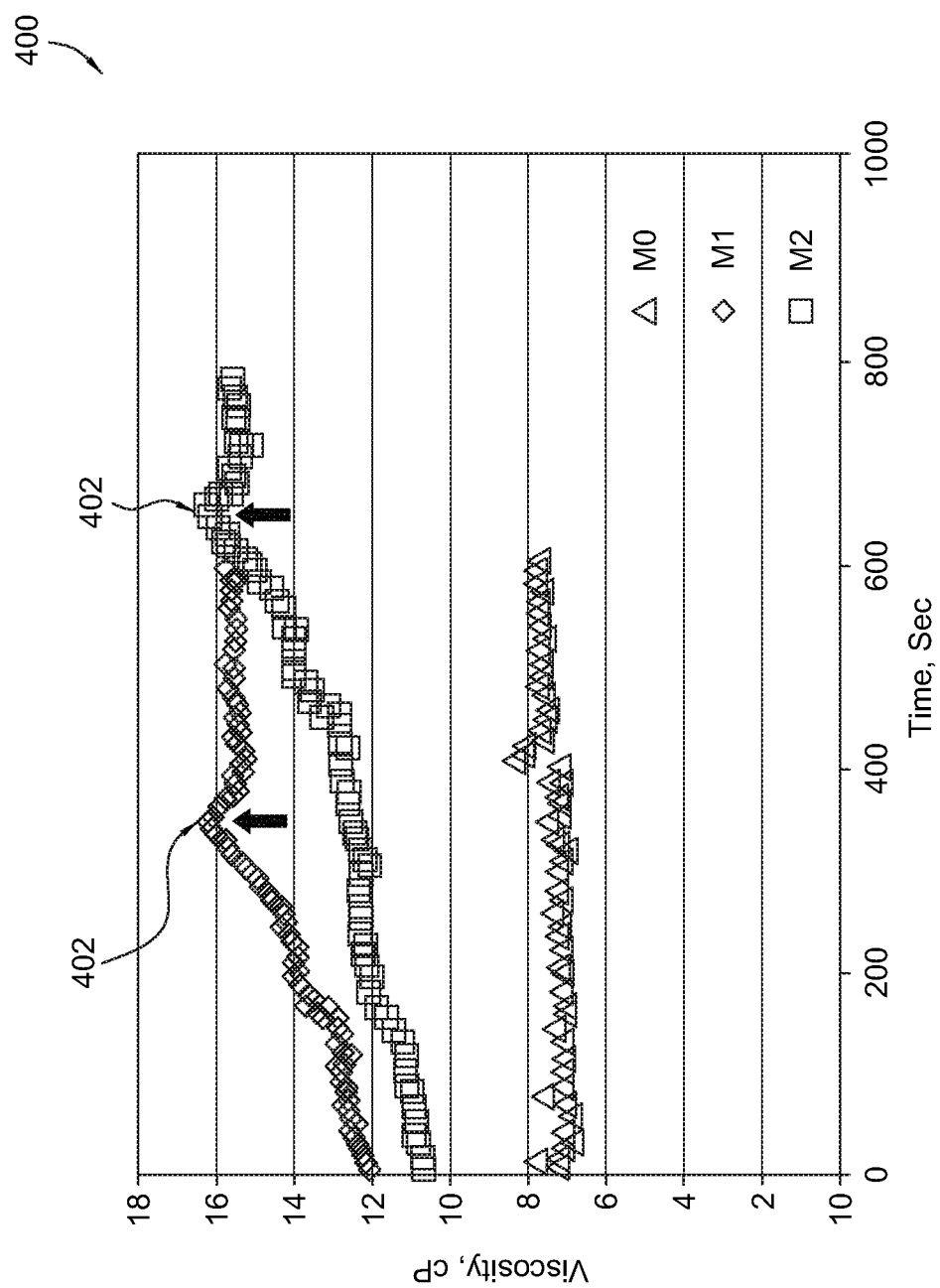
FIG. 4 illustrates example viscosity measurements for an emulsion using the apparatus of FIG. 1. The x-axis is time in seconds, and the y-axis is viscosity in cP.

FIG. 4 illustrates example viscosity measurements 400 for the emulsion using the apparatus of Example 1. The viscosity measurements 400 were obtained for the emulsion using the M0, M1 and M2 configurations of the rotor member. The viscosity measurements 400 were obtained at a shear rate of about 1500 $S^{-1}$. As can be seen from the example graph 402, the measured viscosities using the M1 and M2 configurations with the threads increased with the mixing time and attained at a stable value of about 16 cP (represented by reference numeral 404) that was higher as compared to viscosity measured using the M0 configuration (about 8 cP).

The reverse threading on the rotor member for M1 and M2 configurations guided the two phases of the emulsion in opposite directions toward the fluid interface that facilitated enhanced mixing of the phases.

Figure 5:
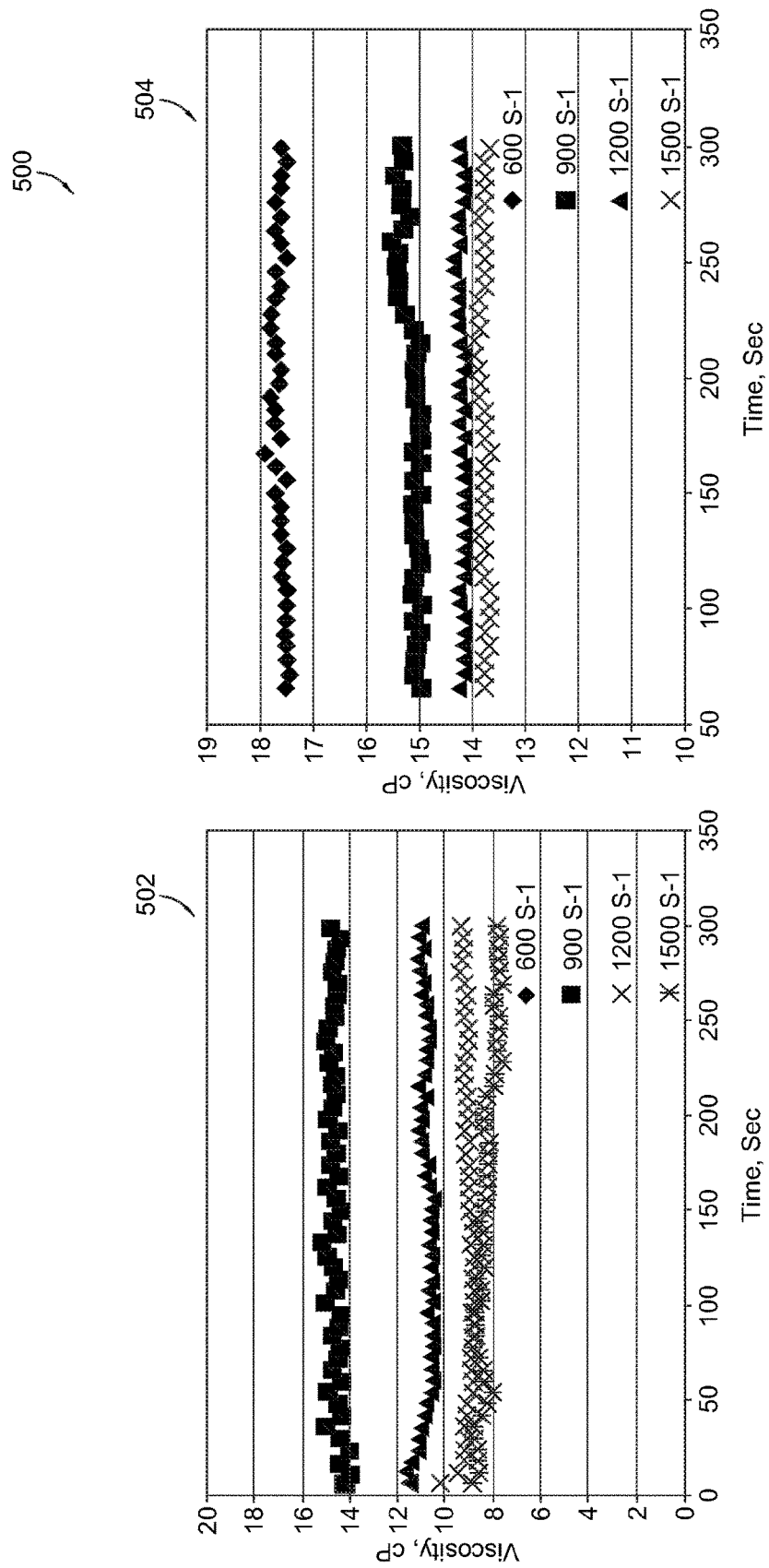
FIG. 5 is a graphical representation of measured viscosity of the emulsion with varying water cut percentage and shear rates applied using the apparatus of FIG. 1. The x-axis is time in seconds, and the y-axis is viscosity in cP.

FIG. 5 is a graphical representation 500 of viscosity variation of the emulsion for different shear values. The viscosity variations measured for the configurations M0 and M2 for varying shear rates (600 $S^{-1}$, 900 $S^{-1}$, 12000 $S^{-1}$, 1500 $S^{-1}$) are represented by reference numerals 502 (configuration M0; FIG. 5A) and 504 (configuration M2; FIG. 5B) respectively. Here, a rate of mixing of the fluids was determined by the slope of the viscosity variation with time. A desired rate of mixing of the fluids was achieved by adjusting parameters such as pitch and depth of the threads of the rotor member. Further, the measured viscosity of the emulsion was measured to be substantially same (about 16 cP) for the configurations M1 and M2 having different thread parameters that was indicative of achieving a stable viscosity measurement with different thread configurations of the rotor member. Moreover, the degree of mixing and the viscosity measurements observed for threaded rotor configurations M1 and M2 were substantially the same thereby indicating the repeatability of measurements using such threaded configurations.

Example 4

Results of CFD Simulations

Here three-dimensional (3D) simulations were performed using threaded and un-threaded rotor members for liquids having different densities. In this simulation, engine oil and water were introduced in the static chamber and the rotor member was rotated at about 60 rpm. It was observed that a degree of mixing achieved for the un-threaded rotor member was about 10% at time period of about 3 seconds. Moreover, for a right-hand threaded rotor member, the degree of mixing was computed to be about 50% at time period of about 3.5 seconds from onset of mixing. In addition, the degree of mixing for a reverse threaded rotor member was computed to be about 80% at time period of about 3.5 seconds from onset of mixing. As can be seen, the threaded rotor member enabled efficient mixing of the fluids as compared to that achieved by the un-threaded rotor member.

Example 5

A Kit to Measure Rheological Parameters of a Multi-Phase Fluid

A kit for measuring the rheological parameters of a multi-phase fluid was formed. The kit included a rotor member having at least a first portion and a second portion with a first set of threads and a second set of threads formed thereon respectively. The first set of threads and the second set of threads were oppositely angled and were configured to apply a shear stress to a first phase and a second phase of a multi-phase fluid as the rotor member was rotated inside the static chamber containing the multi-phase fluid. The first portion and the second portion of the rotor member were substantially submersed in the first phase and the second phase of the multi-phase fluid respectively. The kit further included a processing circuitry which was configured to estimate rheological parameters of the multi-phase fluid based on applied shear rate, temperature of the multi-phase fluid, pressure of the multi-phase fluid or combinations thereof.

Example 6

Configuration of an Apparatus for Measuring Rheological Parameters of a Multi-Phase Fluid In another example, different sizes of the static chamber and the rotor member were used for measuring the rheological parameters of another multi-phase fluid with a different viscosity. The static chamber had a length of about 75 mm and a diameter of the static chamber was about 75 mm. The dimensions of the rotor member with the details of the threads formed on the rotor member are provided in Table 2. A standard geometry of the rotor member (represented here by M0') was obtained and used for obtaining viscosity measurements. Further, five configurations of the rotor member (represented by M1', M2', M2-R, M3' and M4 respectively) having different thread pitch and width were designed. The rotor member was formed of stainless steel-316. The configurations M1' to M4' were reverse threaded configurations, except M2-R. Unlike M2-R, the configurations M1' to M4' were threaded in such a way that the threads/flows were directed inwards from phase changing line, when rotated in the anticlockwise direction.

TABLE 2

| Sr. No. | Rotor member length, L, mm | Rotor member diameter, D, mm | $L_1$, mm | Angle, $\theta$ | Half length from top, $L_2$ | Pitch, mm | Pitch Depth, d, mm | Nomenclature used | Sr. No. |
|---|---|---|---|---|---|---|---|---|---|
| 1. | 38 | 25 | 07 | 30° | — | — | — | — | M0, |
| 2. | 38 | 25 | 07 | 30° | 19 | — | 0.5 | 0.5 | M1, |
| 3. | 38 | 25 | 07 | 30° | 19 | — | 1.5 | 1.0 | M2, |
| 4. | 38 | 25 | 07 | 30° | 19 | — | 1.5 | 1.0 | M2-R |
| 5. | 38 | 25 | 07 | 30° | 19 | — | 3.0 | 2.0 | M3, |
| 6. | 38 | 25 | 07 | 30° | 13 | 12 | 1.5 | 1.0 | M4, |

The five configurations (M0', M1', M2', M2-R, M3' and M4') of the rotor member were used to measure rheological parameters of emulsions. The comparative results for the measurements for the configurations are discussed below.

Example 7

Viscosity Measurements of Emulsions Using the Apparatus of Example 1a

The different configurations provided in Table 2 were used to measure the rheological parameters of emulsions. The viscosity of the water based fluid and oil based fluid were measured using standard geometry, M0' and observed to be, 44.28 cP, and, 199.55 cP, respectively. The two fluids were subsequently used to create in-situ emulsion in the annular space between the static chamber and the rotor member. A 12 mL sample was used for the measurements. A volume percentage of about 50:50 of the water base fluid and oil base fluids was used to form the multi-phase fluid for measurement of viscosity of the multi-phase fluid.

Example 8

Results of Viscosity Measurements of the Emulsion with Varying Shear Rates Applied Using the Rotor Members of Example 6

Figure 6:
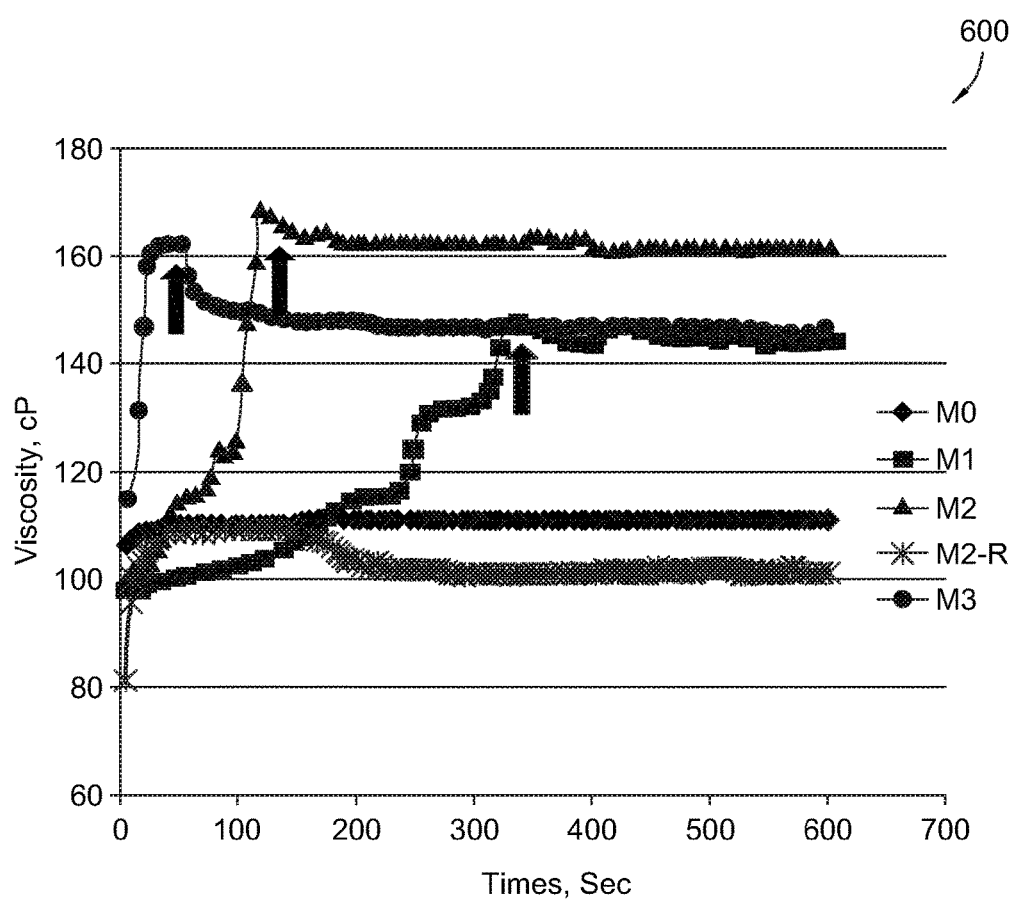
FIG. 6 is a graphical representation of measured viscosity of the emulsion at a shear rate of 1500 $S^{-1}$ using the configurations provided in Table 2. The x-axis is time in seconds, and the y-axis is viscosity in cP.

FIG. 6 illustrates example viscosity measurement 600 for the emulsion using the configurations provided in Table 2. The viscosity measurements 600 were obtained for the emulsion using M0', M1', M2', M2-R and M3' configurations of the rotor member. The viscosity measurements 600 were obtained at a shear rate of about 1500 $S^{-1}$. As can be seen from the example graph 602, the viscosity of the emulsion was observed to be 146 cP using M1' and M3' configurations, while it was 162 cP using M2' configuration. This was well within the deviation of about 10% for M1'/M3' configuration than M2' configuration. It is expected that finer the thread size, better the mixing for lower viscous fluids and broader the thread size, better the mixing for higher viscous fluid. The time taken to mix the two phases (as indicated by arrow in FIG. 6) were observed to be 143, 168 and 162 sec for M1', M2' and M3', respectively. This demonstrated that with the increasing thread size, the time taken to mix the fluid decreased. M2-R configuration did not result any emulsion and was very poor in handling the multiphase system. M2-R configuration was threaded in reverse direction. The threading pulled apart the two phase while mixing, but as the annular space was very small (of the order of 1 mm), the movement of fluid element in such small annular space was restricted resulting in very poor mixing for M2-R configuration. The M0' configuration, as expected, did not show any mixing, and was evident from the no change in the data of viscosity for various times.

Example 9

Results of Viscosity Measurements of the Emulsion with Varying Shear Rates Applied Using the Rotor Members M4'

Figure 7B:
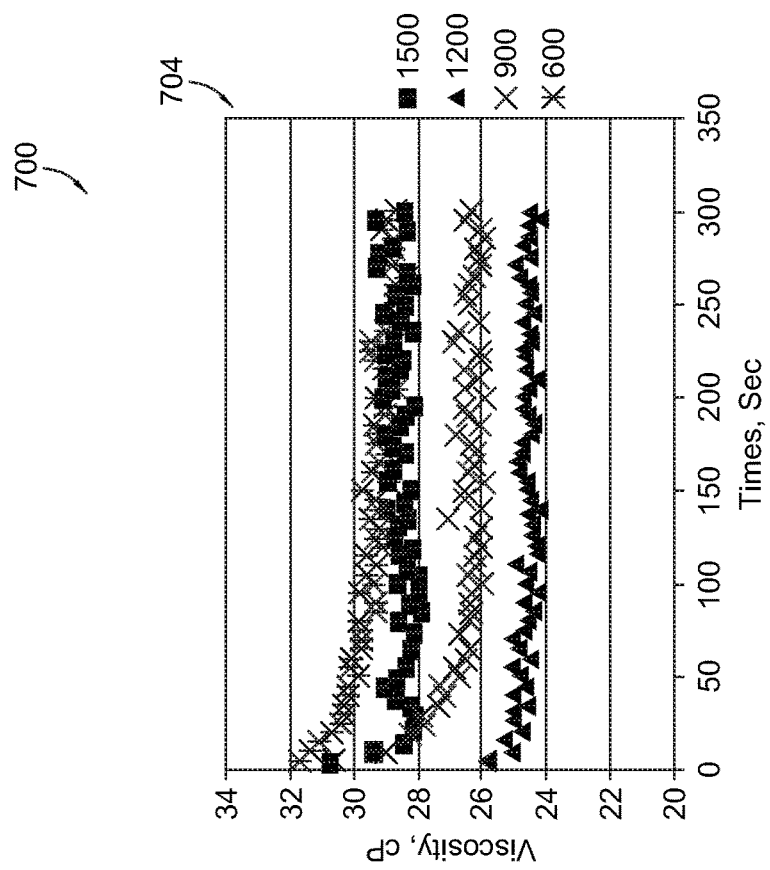
FIG. 7b is a graphical representation of measured viscosity of the emulsion at varying shear rates applied using the configuration M4'. The x-axis is time in seconds, and the y-axis is viscosity in cP.
Figure 7A:
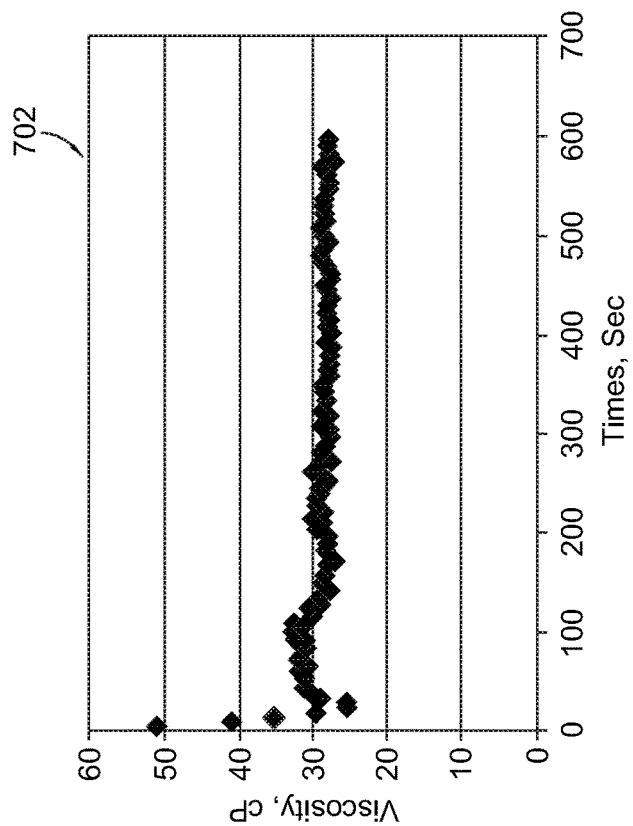
FIG. 7a is a graphical representation of measured viscosity of the emulsion at a shear rate of 1500 S$^{-1}$ using the configuration M4'. The x-axis is time in seconds, and the y-axis is viscosity in cP.

The three phase configuration, M4' as shown in FIG. 3 was used to study the three phase system containing lube diesel, lube oil, and water base fluid. As shown in FIG. 7a, the mixing with configuration M4' resulted in a stable emulsion. The viscosity of emulsion decreased in the first 30 seconds due to the mixing of lube oil with diesel, resulting in decrease in the overall viscosity, and subsequently the viscosity increased as the combined phase of lube oil and diesel mixed with water base fluid giving another mixing. Thereafter, the viscosity was stable at about 30 cP. Two mixing phenomena occurred, the first mixing being that of the lube oil and diesel decreasing the viscosity followed by mixing the same with water base fluid. FIG. 7b illustrates the viscosity of the emulsion at varying shear rate. The data confirmed the non-Newtonian behavior of the three phase system.

The threaded configurations resulted in better mixing compared to a standard geometry. M1', M2' and M3' resulted in higher viscosities than M0', justifying the fact that the threading on the surface of the configuration improved the mixing while measuring the viscosity. The threading reduced the drawback of conventional geometry and also the requirement of an additional mixer pre-measurement. In case of M2-R configuration, where the direction of the threading is reversed (opposite), the mixing was poor.

Further, the pitch size was observed to affect the time required for mixing, and thus, showed applications for varying systems of multiphase combinations. The parameters such as diameter, length and pitch size of the configurations can be varied to address different ranges of viscosities.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed herein also encompass any and all possible sub ranges and combinations of sub ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc.

As will also be understood by one skilled in the art all language such as "up to," "at least," "greater than," "less than," and the like include the number recited and refer to ranges which can be subsequently broken down into sub ranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. An apparatus for measuring rheological parameters of a multi-phase fluid, the apparatus comprising:
   a static chamber containing a multi-phase fluid having at least a first phase and a second phase; and
   a rotor member submersed in the multi-phase fluid in the static chamber and rotatable about a rotational axis within the static chamber, wherein the rotor member comprises a first set of threads formed on a first portion of the rotor member submersed in the first phase of the multi-phase fluid and a second set of threads formed on a second portion of the rotor member submersed in the second phase of the multi-phase fluid, wherein the first phase of the multi-phase fluid is disposed above the second phase of the multi-phase fluid, wherein the first set of threads is disposed above the second set of threads, and wherein a pitch and a depth of the first set of threads and the second set of threads are selected based upon a density and viscosity of each of the first phase and the second phase of the multi-phase fluid, a required degree of mixing, or combinations thereof.

2. The apparatus of claim 1, wherein the static chamber and the rotor member are coaxial.

3. The apparatus of claim 1, wherein the static chamber is formed of stainless steel, hastelloy, or combinations thereof.

4. The apparatus of claim 1, wherein the rotor member is formed of stainless steel, hastelloy, or combinations thereof.

5. The apparatus of claim 1, wherein at least one of the first set of threads and the second set of threads comprises acme threads, buttress threads, whitworth threads, V-threads, or combinations thereof.

6. The apparatus of claim 1, wherein the first phase of the multi-phase fluid is a liquid and the second phase of the multi-phase fluid is a gas.

7. The apparatus of claim 1, wherein the first phase of the multi-phase fluid is a solid and the second phase of the multi-phase fluid is a liquid.

8. The apparatus of claim 1, wherein the first phase of the multi-phase fluid is a liquid, second phase of the multi-phase fluid is a solid and a third phase of the multi-phase fluid is a gas.

9. The apparatus of claim 1, wherein the static chamber and the rotor member define a shear zone containing the multi-phase fluid, wherein a shear stress is applied to the multi-phase fluid by rotating the rotor member.

10. The apparatus of claim 1, wherein a pitch of the first set of threads and the second set of threads is about 0.1 mm to about 25 mm.

11. The apparatus of claim 1, wherein a ratio of pitch to a length of the first set of threads and the second set of threads is about 0.01 to 0.5.

12. The apparatus of claim 1, wherein a depth of the first set of threads and the second set of threads is about 0.1 mm to about 25 mm.

13. The apparatus of claim 1, wherein the ratio of depth to the diameter of the first set of threads and second set of threads is about 0.01 to 0.5.

14. The apparatus of claim 1, wherein a degree of mixing of the first phase and the second phase is about 1% to about 99%.

15. The apparatus of claim 1, wherein the multi-phase fluid comprises at least two immiscible fluids.

16. The apparatus of claim 15, wherein the multi-phase fluid comprises oil and water.

17. The apparatus of claim 1, further comprising a processing circuitry configured to estimate the rheological parameters of the multi-phase fluid based on an applied shear rate, a temperature of the multi-phase fluid, a pressure of the multi-phase fluid, or combinations thereof.

18. The apparatus of claim 17, wherein the rheological parameters of the multi-phase fluid comprise a viscosity, a shear storage modulus, a shear loss modulus, or combinations thereof.

19. The apparatus of claim 1, wherein the first set of threads and the second set of threads are oppositely angled.

20. The apparatus of claim 10, wherein a thread angle of the first set of threads is about 5 degrees to about 70 degrees.

21. The apparatus of claim 10, wherein a thread angle of the second set of threads is between 5 degrees and 70 degrees.

22. The apparatus of claim 1, further comprising a motor configured to rotate the rotor member about the rotational axis.

23. The apparatus of claim 22, wherein a speed of rotation of the rotor member is about 0.01 rpm to about 10000 rpm.

24. The apparatus of claim 22, wherein an applied shear rate is about $10^{-5}$ $S^{-1}$ to about $10^7$ $S^{-1}$.

25. An apparatus for measuring rheological parameters of a multi-phase fluid, the apparatus comprising:
a static chamber containing a multi-phase fluid having at least a first phase and a second phase;
a rotor member submersed in the multi-phase fluid in the static chamber and rotatable about a rotational axis within the static chamber to apply a shear stress to the multi-phase fluid, wherein the rotor member comprises a first portion having a first set of threads formed thereon in a first direction and a second portion having a second set of threads formed thereon in a second direction that is opposite to the first direction; and
a processing circuitry configured to estimate the rheological parameters of the multi-phase fluid as the rotor member is rotated within the static chamber,
wherein the first phase of the multi-phase fluid is disposed above the second phase of the multi-phase fluid, and wherein the first set of threads is disposed above the second set of threads,
and wherein a height of the first portion and a height of the second portion of the rotor member are determined based upon a volume of the first phase and a volume of the second phase respectively.

26. The apparatus of claim 25, wherein the first portion and the second portion of the rotor member are substantially submersed in the first phase and the second phase of the multi-phase fluid respectively.

27. The apparatus of claim 25, wherein the multi-phase fluid comprises a third phase.

28. The apparatus of claim 27, wherein the rotor member comprises a third un-threaded portion disposed between the first portion and the second portion, wherein the third un-threaded portion is substantially submersed in the third phase of the multi-phase fluid.

29. A method for measuring rheological parameters of a multi-phase fluid, the method comprising:
providing a static chamber having a rotor member, wherein the rotor member comprises a first portion having a first set of threads formed thereon in a first direction and a second portion having a second set of threads formed thereon in a second direction that is opposite to the first direction;
placing a multi-phase fluid having a first phase and a second phase within the static chamber such that the first portion and the second portion of the rotor member are substantially submersed in the first phase and the second phase of the multi-phase fluid respectively; and
rotating the rotor member about a rotational axis to apply shear stress to the first phase and the second phase of the multi-phase fluid through the first set of threads and the second set of threads respectively,
wherein the first phase of the multi-phase fluid is disposed above the second phase of the multi-phase fluid, and wherein the first set of threads is disposed above the second set of threads,
and wherein a height of the first portion and a height of the second portion of the rotor member are determined based upon a volume of the first phase and a volume of the second phase respectively.

30. The method of claim 29, wherein a pitch and a depth of the first set of threads and the second set of threads are selected based upon a density and viscosity of each of the first phase and the second phase of the multi-phase fluid, a required degree of mixing, or combinations thereof.

31. The method of claim 29, wherein rotating the rotor member comprises driving the first phase and the second phase of the multi-phase fluid towards an interface of the first portion and the second portion of the rotor member to facilitate mixing of the first phase and the second phase.

* * * * *